(12) United States Patent
Nowlan, III

(10) Patent No.: US 11,298,308 B1
(45) Date of Patent: Apr. 12, 2022

(54) HAIR BLEACHING COMPOSITIONS AND METHODS OF USE

(71) Applicant: ELC Management LLC, Melville, NY (US)

(72) Inventor: Daniel Thomas Nowlan, III, Hugo, MN (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 17/320,150

(22) Filed: May 13, 2021

(51) Int. Cl.
| | |
|---|---|
| *A61Q 5/08* | (2006.01) |
| *A61K 8/60* | (2006.01) |
| *A61K 8/23* | (2006.01) |
| *A61K 8/49* | (2006.01) |
| *A61K 8/44* | (2006.01) |

(52) U.S. Cl.
CPC ............ *A61K 8/602* (2013.01); *A61K 8/23* (2013.01); *A61K 8/44* (2013.01); *A61K 8/4913* (2013.01); *A61Q 5/08* (2013.01); *A61K 2800/4324* (2013.01); *A61K 2800/882* (2013.01)

(58) Field of Classification Search
CPC ... A61Q 5/08; A61K 8/22; A61K 8/23; A61K 2800/882; A61K 8/44
USPC .......................................................... 424/62
See application file for complete search history.

(56) References Cited

U.S. PATENT DOCUMENTS

| | | | |
|---|---|---|---|
| 9,498,419 B2 | 11/2016 | Pressly et al. | |
| 2004/0247551 A1* | 12/2004 | Yokomaku | A61K 8/73 424/70.13 |
| 2016/0128915 A1* | 5/2016 | Konno | B65D 83/68 424/62 |
| 2017/0340549 A1 | 11/2017 | Anderheggen et al. | |
| 2017/0340553 A1 | 11/2017 | Anderheggen et al. | |
| 2018/0116930 A1 | 5/2018 | Degeorge et al. | |
| 2018/0008524 A1 | 8/2018 | Anderheggen et al. | |

FOREIGN PATENT DOCUMENTS

| | | |
|---|---|---|
| CN | 101500536 B | 12/2011 |
| EP | 2301520 B1 | 3/2017 |
| JP | 2004-035529 A | 2/2004 |
| JP | 2006-083130 A | 3/2006 |

OTHER PUBLICATIONS

Eiko Oshimura et al; "Hair and amino acids: The interactions and the effects"; AminoScience Laboratory, Ajlnomoto Co., Inc.; Suzuki-cho 1-1, Kawasaki 210-8681, Japan; J. Cosmet. Sci., 58, 347-357 (Jul./Aug. 2007).

Mintel; GNPD; Armored Straightining; Record ID: 1209282; IMS; IMS; Amora do Campo; Hair Products; Hair Treatments; Brazil; Nov. 2009.

Mintel; GNPD; Day Cream Face Cream; Record ID: 4027427; Creative Cosmetic Agency; Creative Cosmetic Agency; Dr. Sebagh Supreme; Skincare; Face/Neck Care; UK; France; Jun. 2016.

Yuichi Nishida et al.; "Repairing Effects of Diglusoyl Gallic Acid on Coloring-Damaged Hair"; J. Oleo Sci., vol. 53, No. 6, 295-304 (2004).

* cited by examiner

*Primary Examiner* — Eisa B Elhilo
(74) *Attorney, Agent, or Firm* — Yonggang Wu

(57) ABSTRACT

Hair bleaching compositions, methods for using hair bleaching compositions, and methods for preparing hair bleaching compositions are provided herein. The hair bleaching compositions comprise at least one gallic acid derivative, at least one amino acid and/or at least one amino acid derivative, at least one oxidizing agent, and optionally, at least one hair care agent and/or hair treatment agent.

9 Claims, No Drawings

HAIR BLEACHING COMPOSITIONS AND METHODS OF USE

FIELD OF THE INVENTION

The present invention generally relates to compositions and methods for bleaching hair, and methods for preparing hair bleaching compositions.

BACKGROUND OF THE INVENTION

Hair coloring, a process of changing the hair color, is widely employed to achieve desirable hair colors and used as a major hair styling tool. The hair coloring process typically includes steps of bleaching the hair and then depositing the desired color onto the hair. The purpose of beaching the hair is to rid the hair off its current color so later deposited colors could present optimal effects. In majority of the cases, the bleaching step is mandatory because the residue of the current hair color would interfere with the later deposited color and render it impossible to achieve desirable end effects. This beaching step is known as hair "lightening" or hair color "lifting" step and plays a vital role in hair coloring and styling industry.

Hair bleaching has its drawbacks, mainly due to the oxidative ingredients employed in the hair bleaching process. These oxidative ingredients are known to cause damages to the hair and/or irritate the scalp. The damages caused by hair bleaching may be not only cosmetic but also structural. For example, the hair bleaching process could result in breakage of the disulfide bonds in hair fibres. In turn, hair bleaching becomes a major limiting step in hair coloring and hair styling.

Despite of the industry's long-time effort in search for methods to remediate and minimize the hair damage caused by hair bleaching, nothing has fundamentally solved this issue yet. The researchers have taken two different approaches in addressing this issue: after-bleaching remedial treatments and new damage-minimizing bleaching methods. The former has been limited by the fact that some structural damages are permanent and simply cannot be cured by remedial treatments. The latter, new damage-minimizing bleaching method, has posed significant challenges because the main contributors of the hair damages, the oxidative ingredients, must be also potent enough to effectively bleach the hair. Thus, a perfect balance must be struck to achieve an ideal bleaching method, where the hair fibre is significantly strengthened against the bleaching damage during the bleaching process and at the same time it will maintain reasonable bleaching potential.

Thus, one objective of the disclosure is to provide hair bleaching compositions that are unexpectedly gentle toward the hair while at the same time maintain reasonable bleaching efficacies.

SUMMARY OF THE INVENTION

Hair bleaching compositions, method for using hair bleaching compositions, and method for preparing hair bleaching compositions are provided herein.

The invention is directed to hair bleaching compositions comprising (a) at least one gallic acid derivative; (b) at least one amino acid and/or at least one amino acid derivative; (c) at least one oxidizing agent; and (d) optionally, at least one hair care agent and/or hair treatment agent.

The invention is also directed to methods for using hair bleaching compositions, comprising (a) mixing the hair bleaching composition with a developer composition; (b) applying the mixture of the step (a) onto hair and allowing the mixture to remain for no more than two hours; (c) rinsing the mixture of the step (a) from hair; wherein the hair bleaching composition comprises at least one gallic acid derivative, at least one amino acid and/or at least one amino acid derivative, at least one oxidizing agent, and optionally, at least one hair care and/or hair treatment agent.

The invention is also directed to methods for preparing hair bleaching compositions, comprising (a) mixing one or more gallic acid derivatives with one or more amino acids and/or cosmetically acceptable salts thereof; and (b) mixing bleaching agents with the mixture of the step (a) to form the hair bleaching composition; wherein the hair bleaching compositions is freshly prepared for hair bleaching.

DETAILED DESCRIPTION OF THE INVENTION

Definitions and Conventions

The term, "comprising" means that a list of elements is not necessarily limited to those explicitly recited.

As used herein, "hair" means mammalian hair including scalp hair, facial hair and body hair, but particularly hair of the human head.

As used herein, "cosmetically acceptable" means that compositions or components are suitable for use in contact with human keratinous tissue.

As used herein, "naturally occurring" means existing by nature and without artificial aid.

As used herein, "essential amino acid" means amino acid selected from the group consisting of histidine, isoleucine, leucine, lysine, methionine, phenylalanine, threonine, tryptophan, and valine.

As used herein, "conditionally essential amino acid" means amino acid selected from the group of arginine, cysteine, glutamine, tyrosine, glycine, ornithine, proline, and serine.

The term "molecular weight" refers to the weight average molecular weight, unless otherwise stated.

As used herein, "QS" means sufficient quantity for 100%.

As used herein, the phrase "persulfate load" means the weight percentage of the persulfate ion based upon the weight of the total composition.

As used herein, the phrase "percarbonate load" means the weight percentage of the percarbonate ion based upon the weight of the total composition.

Unless otherwise stated: all numerical amounts are understood to be modified by the word "about," all percentages are by weight of the total composition, and all ratios are weight ratios.

It should be understood that every numerical range expressly recited herein will include every narrower numerical range that falls within such broader numerical range, as if such narrower numerical ranges were all expressly recited herein.

As used herein, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means.

As used herein, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C." As another example, the sentence "In some embodiments, the composition comprises at least A, B, or C" is to be interpreted as if written as the following three separate sentences: "In some embodiments, the composition comprises at least A. In some embodiments, the composition comprises at least B. In some embodiments, the composition comprises at least C."

As used herein, "and/or" means "and" or "or". For example, "A and/or B" means "A, B, or both A and B," and "A, B, C, and/or D" means "A, B, C, D, or a combination thereof," and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

Hair Bleaching Composition

Described herein are hair bleaching compositions comprising:

a) at least one gallic acid derivative;

b) at least one amino acid and/or at least one amino acid derivative;

c) at least one oxidizing agent; and d) optionally, at least one hair care agent and/or hair treatment agent.

The hair bleaching compositions may be in the form of powder, slurry powder, suspension, emulsion, cream, lotion, and ointment.

Gallic Acid Derivatives

The hair bleaching compositions comprise at least one gallic acid derivative of the following Formula (I),

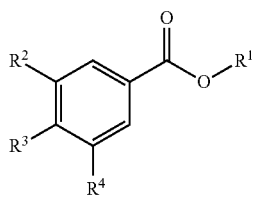

Formula (I)

wherein $R^1$ represents a hydrogen atom, an alkali metal, an alkaline earth metal, an ammonium salt, or an alkyl or alkenyl group having from 1 to 18 carbon atoms; $R^2$, $R^3$, and $R^4$ independently represent a hydrogen atom, an hydroxyl group, an alkoxy group having from 1 to 18 carbon atoms, a polyoxyethylene group, a polyoxypropylene group, or a residue of a monosaccharide, a disaccharide or an oligosaccharide.

Preferably, the hair bleaching compositions may comprise one or more gallic acid derivatives wherein two of $R^2$, $R^3$, and $R^4$ in the formula (I) independently represent a residue of a monosaccharide, disaccharide, or oligosaccharide.

More preferably, the hair bleaching compositions may comprise one or more gallic acid derivative selected from the group of gallic acid-3,5-diglucoside; gallic acid-3,4-diglucoside; methyl gallate-3,5-diglucoside; ethyl gallate-3,5-diglucoside; propyl gallate-3,5-diglucoside; butyl gallate-3,5-diglucoside; gallic acid-3,5-dimannoside; sodium gallate-3,5-diglucoside; and ammonium gallate-3,5-diglucoside.

Most preferably, the hair bleaching compositions may comprise gallic acid-3,5-glucoside.

The hair bleaching compositions may further comprise at least one gallic acid derivative wherein one of $R^2$, $R^3$, and $R^4$ in the formula (I) represents a residue of a monosaccharide, disaccharide, or oligosaccharide, each based on the total content of the gallic acid derivatives. Preferably, the gallic acid derivative wherein one of $R^2$, $R^3$, and $R^4$ represents a residue of a monosaccharide, disaccharide, or oligosaccharide, each based on the total content of the gallic acid derivatives, is selected from the group of gallic acid-3-glucoside, methyl galate-3-glucoside, ethyl galate-3-glucoside, propyl galate-3-glucoside, gallic acid-4-glucoside, sodium gallic acid-3-glucoside, ammonium gallic acid-4-glucoside, gallic acid-3-mannoside, gallic acid-4-mannoside, methyl galate-4-mannoside and the like.

Nonlimiting examples of commercial gallic acid derivatives include the product under the trade name of DGG LEOGARD DGG sold by Lion Specialty Chemicals Co., Ltd., with the INCI name of diglucosyl gallic acid.

The hair bleaching compositions may comprise at least one gallic acid derivative, in a total amount, of 0.0001% to 10%, preferably 0.0005% to 5%, particularly preferably 0.001% to 1%, and exceptionally preferably 0.01% to 0.1%, each based on the weight of the hair bleaching composition.

Amino Acids and Amino Acid Derivatives

The hair bleaching compositions comprise at least one amino acid and/or at least one amino acid derivative.

The at least one amino acid may be selected from the group consisting of alanine, arginine, asparagine, aspartic acid, citrulline, cysteine, glutamic acid, glutamine, glycine, histidine, isoleucine, leucine, lysine, methionine, ornithine, phenylalanine, proline, serine, threonine, tryptophan, tyrosine, valine, and mixtures thereof.

The at least one amino acid may be selected from essential amino acids, conditionally essential amino acids, and mixtures thereof. Preferably, the at least one amino acid may comprise at least one essential amino acid and at least one conditionally essential amino acid.

The at least one amino acid derivative may be naturally occurring amino acid derivatives.

The at least one amino acid derivative may be selected from amino acid salts, lactams, and mixtures thereof.

The at least one amino acid derivative may comprise amino acid salts. Preferably, the amino acid salts may be selected from the group consisting of alkali metal salts, alkaline earth metal salts, ammonium salts, and mixtures thereof. More preferably, the amino acid salts may be alkali metal salts.

The at least one amino acid derivative may comprise lactam. It is understood that some lactams may contain free acid group (i.e., pyroglutamic acid) and thus may possibly form salts (i.e., pyroglutamic salts). Thus when chemically possible, the at least one amino derivative may comprise lactams and/or their salts thereof. Preferably, the at least one amino acid derivative may be selected from the group consisting of β-lactam, γ-lactam, δ-lactam, and ε-lactam. More preferably, the at least one amino acid derivative may comprise γ-Lactam. Most preferably, the at least one amino acid derivative may comprise pyroglutamic acid and/or its salts.

Preferably, the hair bleaching compositions comprise at least one amino acid and at least one amino acid derivative. More preferably, the hair bleaching compositions may comprise at least two amino acids and at least one amino acid derivative. Particularly preferably, the hair bleaching compositions may comprise at least one essential amino acid, at least one conditionally essential amino acid, at least one lactam, and/or their cosmetically acceptable salts thereof. Exceptionally preferably, the hair bleaching compositions comprise lysine, arginine, and pyroglutamic acid, and/or their cosmetically acceptable salts thereof. Most preferably, the hair bleaching compositions comprise lysine, arginine, and pyroglutamic acid.

The hair bleaching compositions may comprise at least one amino acid and/or a least one amino acid derivative, in a total amount, of 0.01% to 10%, preferably 0.05% to 8%, particularly preferably 0.08% to 5%, and exceptionally preferably 0.1% to 3%, each based on the weight of the hair bleaching composition.

When the hair bleaching composition comprises at least one amino acid and at least one lactam, the total weight of present amino acids may be less than the total weight of present lactams. Preferably, the weight ratio of the amino acid with the lowest concentrate to the lactam with the highest concentration may be no less than 1:20, preferably no less than 1:15, more preferably no less than 1:10.

When the hair bleaching composition comprises at least two amino acids, the weight ratio of the amino acid with the highest concentrate to the amino acid with the lowest concentrate may be no greater than 10:1, preferably no greater than 8:1, more preferably no greater than 5:1.

When the hair bleaching composition comprises pyroglutamic acid, lysine, and arginine, and/or their cosmetically acceptable salts thereof, the order from the highest to the lowest concentration may be pyroglutamic acid, arginine, and lysine.

Oxidizing Agents

The hair bleaching compositions comprise at least one oxidizing agent.

The oxidizing agent may be selected from the group consisting of persulfate salts, percarbonate salts, and mixtures thereof.

Preferably, the oxidizing agent may be selected from the group consisting of alkali metal persulfate salts, alkali metal percarbonate salts, ammonium persulfate, ammonium percarbonate, and mixtures thereof.

Examples of persulfate salts include, but are not limited to, sodium persulfate, potassium persulfate, and ammonium persulfate.

Examples of percarbonate salts include, but are not limited to, sodium percarbonate and potassium percarbonate.

More preferably, the hair bleaching compositions comprise at least one persulfate salt.

Most preferably, the hair bleaching compositions comprises at least one persulfate salt selected from the group consisting of sodium persulfate, potassium persulfate, ammonium persulfate, and mixtures thereof.

Oxidizing agents may be used in pure form or in admixture of other ingredients for hair bleaching purposes. Oxidizing mixtures are frequently used in the industry and may contain one or more oxidizing agents. Mixing multiple oxidizing agents may lead to advantageous effects such as better solubility, smoother application, better compliance with developers, and better appearance end results.

Examples of oxidizing mixtures include, but are not limited to, commercially available bleaching powders, for instance the products sold under the trade name Aveda Enlightener Freehand Bond-Strengthening Lightener by Aveda Corporation, and under the trade name Clairol Professional BW2 Powder Lightener by Coty, Inc.

When oxidizing mixtures are used for hair bleaching purposes, the oxidizing capacity of the hair bleaching compositions may be measured by the persulfate load and/or the percarbonate load, regardless which cations are present in the hair bleaching compositions. The persulfate load of an oxidizing mixture may be determined by established analytical methods, including iodometric titration.

The hair bleaching compositions may comprise at least one oxidizing agent, wherein the persulfate load and/or percarbonate load of the hair bleaching composition may be from 1% to 85%, preferably from 5% to 70%, particularly preferably from 10 to 60%, and exceptionally preferably from 30% to 50%, each based on the weight of the hair bleaching composition.

Optional Hair Care and/or Hair Treatment Ingredients

Optionally, the hair bleaching compositions may comprise hair care and/or hair treatment ingredients that are typically used in hair bleaching compositions, at their conventional art-established levels, as long as those ingredients are compatible with the other components and do not detract from the beneficial results delivered by the present invention. Such optional ingredients include oils, fatty acids, fatty alcohols, esters, suspending agents, pH value adjusters, and the like approved for use in hair bleaching formulations.

The oils typically include natural oils and synthetical oils. The natural oils may be preferred.

Nonlimiting examples of natural oils include avocado oil, castor oil, coconut oil, jojoba oil, grapeseed oil, kukui seed oil, olive oil, rose oil, rosemary oil, sunflower oil, sweet almond oil, and tea oil.

The fatty acids typically include saturated fatty acids and unsaturated fatty acids.

The fatty alcohols typically include saturated fatty alcohols and unsaturated fatty alcohols.

The hair bleaching compositions may comprise at least one hair care and/or hair treatment ingredient, present from 0.01% to 30%, preferably from 0.1% to 20%, particularly preferably from 0.2% to 15%, and exceptionally preferably 0.2% to 10%, each based on the weight of the hair bleaching composition.

Methods of Making

Described herein are methods for preparing a hair bleaching composition, comprising:

a) mixing one or more gallic acid derivatives with one or more amino acids and/or cosmetically acceptable salts thereof; and b) mixing bleaching agents with the mixture of the step (a);

wherein the hair bleaching compositions is freshly prepared for hair bleaching.

Methods of Use

Described herein are methods for using a hair bleaching composition, comprising:

a) mixing the hair bleaching composition with a developer composition;

b) applying the mixture of the step (a) onto hair and allowing the mixture to remain for no more than two hours;

c) rinsing the mixture of the step (a) from hair;

wherein the bleaching composition comprising at least one gallic acid derivative; at least one amino acid and/or at least one amino acid derivative; at least one oxidizing agents; and optionally, one or more hair care and/or hair treatment agents.

Developer Compositions

The developer compositions used in the hair bleaching methods herein comprises hydrogen peroxide and/or peroxide salts.

The developer compositions may comprise hydrogen peroxide and/or peroxide salts by weight, from 0.1% to 50%, preferably from 1% to 30%, each based on the weight of the developer composition.

The purpose of the developer composition is to enable the access to the hair cuticle so hair bleaching and/or coloring can be effective. Without the developer composition, hair bleaching and/or coloring compositions will not achieve the desired results.

The developer strength of a developer composition typically is measured in volumes of oxygen liberated per volume of solution. For example, one volume of a 30 volume developer composition is able to liberate 30 volumes of oxygen.

Examples of developer compositions include, but are not limited to, commercially available products sold under the trade name Aveda Color Catalyst Developer, and under the trade name Salon Care Clear Developer, with various volume selections.

EXAMPLES

The following are non-limiting examples of the hair bleaching compositions described herein. These examples are not to be construed as limitations of the invention, as many variations thereof are possible without departing from the spirit and scope of the invention.

Example 1

1.1. Oxidizing Mixtures

Commercial available oxidizing mixtures were used in the following examples. The persulfate load of each commercial available oxidizing mixture was calculated based on available data or determined by iodometric titration. For example, Aveda Enlightener Freehand Bond-Strengthening Lightener contains about 38% potassium persulfate, about 14% ammonium persulfate, and about 6% sodium persulfate, which can be converted to about 48.5% persulfate load.

TABLE 1

Persulfate Load of Commercially Available Oxidizing Mixtures

| Oxidizing Mixture | Persulfate Load (%) |
| --- | --- |
| Aveda Enlightener Freehand Bond-Strengthening Lightener | 48.5 |
| Clairol Professional BW2 Powder Lightener | 45 |

1.2. Hair bleaching Compositions

The hair bleaching composition of Formula 1 was prepared by mixing 96 gram of Aveda Enlightener Freehand Bond-Strengthening Lightener sold by Aveda Corporation and 4 gram of water.

The hair bleaching composition of Formula 2 was prepared in two steps: at the first step, 80 gram of pyroglutamic acid, 40 gram of arginine, 10 gram of lysine, and 2 gram of diglucosyl gallic acid were mixed together; and at the second step, 1.32 gram of the mixture resulted at the first step was mixed with 96 gram of Aveda Enlightener Freehand Bond-Strengthening Lightener and 2.68 gram of water.

Therefore, based on the persulfate load of the Aveda Enlightener Freehand Bond-Strengthening Lightener Powder, the persulfate loads of Formula 1 and Formula 2 are the same, about 46.56%.

1.3. Application

Tress Preparation

For Experiments I-IV a level 8 hair swatch measuring 1" wide, 6" length", and approximately 3 g of hair was divided into three equivalent sections. One section was retained as the untreated and the other two were used in the Experiments I & III, and Experiments II & IV, respectively.

Experiment I

The hair bleaching composition of Formula 1 (5 g) and Aveda Color Volume 40 Catalyst Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was done once. The treated hair fibres showed sufficient color loss. The treated hair fibres were then stored for 24 hours in a humidity chamber before the Elastic Modulus tests and being used in Experiment III.

Experiment II

The hair bleaching composition of Formula 2 (5 g) and Aveda Color Volume 40 Catalyst Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was done once. The treated hair fibres showed sufficient color loss. The treated hair fibres were then stored for 24 hours in a humidity chamber before the Elastic Modulus tests and before being used for Experiment IV.

Experiment III

The hair bleaching composition of Formula 1 (5 g) and Aveda Color Volume 30 Catalyst Developer (10 g) were mixed. The freshly produced mixture was evenly applied to dry strands of the hair tress from Experiment I at the amount of 5 g of mixture per gram of hair. Once the strands had been bleached for 45 minutes at 37° C., they were washed for 2 minutes using water and dried using a hairdryer on medium heat.

As expected, all treated hair fibres showed more color loss than ones in Experiment I. The treated hair fibres were stored for 24 hours in a humidity chamber before the Elastic Modulus tests.

Experiment IV

The hair bleaching composition Formula 2 (5 g) and the Aveda Color Volume 30 Catalyst Developer (10 g) were mixed. The freshly produced mixture was evenly applied to dry strands of hair the hair tress from Experiment II at the amount of 5 g of mixture per gram of hair. Once the strands had been bleached for 45 minutes at 37° C., they were washed for 2 minutes using water and dried using a hairdryer on medium heat.

All treated hair fibres showed more color loss than the ones in Experiment II. The treated hair fibres were stored for 24 hours in a humidity chamber before the Elastic Modulus tests.

1.4. Determination of Changes in Elastic Modulus (EMod)

From each tress 40 individual hair fibres were prepared for tensile analysis using brass crimps and a Diastron AAS 1600 (Diastron Ltd, UK) to thread and crimp the hair. The mean cross-sectional area of each fibre was determined using a laser micrometer FDAS 770 unit (Diastron Ltd, UK) at 24° C. and 55% relative humidity (RH).

All hair fibres were soaked for 1 hour in water before the test. They then were stretched (0-1.5% extension) with a Diastron MTT 686 instrument with control unit UV1000 (Diastron Ltd, UK) and the final results were calculated by software analysis (UvWin 2.35.0000, Diastron, Ltd, UK). The changes in Elastic Modulus then were recorded in the following table. It is understood that higher EMod value corresponds to stronger hair fibres. Thus the negative EMod value may be related to lower hair fibre strength resulted from the hair lightening process. The more negative the value is, the more strength loss may be caused during the hair lightening process.

The results in Table 2 clearly indicate that hair fibres in Experiment II and IV show much less strength loss than that of hair fibres treated in Experiment I and III, respectively.

TABLE 2

Changes in Elastic Modulus (EMod) Before and After Bleaching

| | Experiment I | Experiment II | Experiment III | Experiment IV |
|---|---|---|---|---|
| ΔEMod (GPa) | −0.9 | −0.7 | −1.4 | −1.1 |

Example 2

2.1 Application

Tress Preparation

For Experiments V and VI a level 8 hair swatch measuring 1" wide, 6" length", and approximately 3 g of hair (IHIP, NY) was divided into three equivalent sections. One section was retained as untreated and the other two were treated as described.

Experiment V

The hair bleaching composition of Formula 1 (5 g) and Aveda Color Volume 40 Catalyst Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was repeated once so that the strands were bleached a total of two times in succession. The treated hair fibres were stored for 24 hours in a humidity chamber before the Elastic Modulus tests. All treated hair fibres showed sufficient color loss.

Experiment VI

The hair bleaching composition of Formula 2 (5 g) and Aveda Color Volume 40 Catalyst Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was repeated once so that the strands were bleached a total of two times in succession. The treated hair fibres were stored for 24 hours in a humidity chamber before the Elastic Modulus tests. All treated hair fibres showed sufficient color loss.

2.2. Determination of Changes in Elastic Modulus (EMod)

From each tress 40 individual hair fibres were prepared for tensile analysis using brass crimps and a Diastron AAS 1600 (Diastron Ltd, UK) to thread and crimp the hair. The mean cross-sectional area of each fibre was determined using a laser micrometer FDAS 770 unit (Diastron Ltd, UK) at 24° C. and 55% relative humidity (RH).

All hair fibres were soaked for 1 hour in water before the test. They then were stretched (0-1.5% extension) with a Diastron MTT 686 instrument with control unit UV1000 (Diastron Ltd, UK) and the final results were calculated by software analysis (UvWin 2.35.0000, Diastron, Ltd, UK). The changes in Elastic Modulus then were recorded in the following table. It is understood that higher EMod value corresponds to stronger hair fibres. Thus the negative EMod value may be related to lower hair fibre strength resulted from the hair lightening process. The more negative the value is, the more strength loss may be caused during the hair lightening process. The results in Table 3 clearly indicate that hair fibres in Experiment VI show much less strength loss than that of hair fibres treated by Experiment V, respectively.

TABLE 3

Changes in Elastic Modulus (EMod) Before and After Bleaching

| | Experiment V | Experiment VI |
|---|---|---|
| ΔEMod (GPa) | −1.21 | −1.08 |

Example 3

3.1 Application

Tress Preparation

For Experiments VII and VIII a level 4 single source hair swatch measuring 1" wide, 6" length", and approximately 3 g of hair (IHIP, NY) was divided into three equivalent sections. One section was retained as untreated and the other two were treated as described.

Experiment VII

The hair bleaching composition of Formula 1 (5 g) and Aveda Color Volume 30 Catalyst Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was repeated once so that the strands were bleached a total of two times in succession. The treated hair fibres were stored for 24 hours in a humidity chamber before the Elastic Modulus tests. All treated hair fibres showed sufficient color loss.

Experiment VIII

The hair bleaching composition of Formula 2 (5 g) and Aveda Color Volume 30 Catalyst Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was repeated once so that the strands were bleached a total of two times in succession. The treated hair fibres were stored for 24 hours in a humidity chamber before the Elastic Modulus tests. All treated hair fibres showed sufficient color loss.

3.2. Determination of Changes in Elastic Modulus (EMod)

From each tress 40 individual hair fibres were prepared for tensile analysis using brass crimps and a Diastron AAS 1600 (Diastron Ltd, UK) to thread and crimp the hair. The mean cross-sectional area of each fibre was determined using a laser micrometer FDAS 770 unit (Diastron Ltd, UK) at 24° C. and 55% relative humidity (RH).

All hair fibres were soaked for 1 hour in water before the test. They then were stretched (0-1.5% extension) with a Diastron MTT 686 instrument with control unit UV1000 (Diastron Ltd, UK) and the final results were calculated by software analysis (UvWin 2.35.0000, Diastron, Ltd, UK). The changes in Elastic Modulus then were recorded in the following table. It is understood that higher EMod value corresponds to stronger hair fibres. Thus the negative EMod value may be related to lower hair fibre strength resulted from the hair lightening process. The more negative the value is, the more strength loss may be caused during the hair lightening process.

The results in Table 4 clearly indicate that hair fibres in Experiment VIII show much less strength loss than that of hair fibres treated by Experiment VII, respectively.

TABLE 4

Changes in Elastic Modulus (EMod) Before and After Bleaching

|  | Experiment VII | Experiment VIII |
|---|---|---|
| ΔEMod (GPa) | −1.3 | −1.1 |

Example 4

4.1 Hair Bleaching Composition

The hair bleaching composition of Formula 3 was prepared by mixing 98.6 gram of Clairol Professional BW2 Powder Lightener by Coty, Inc. and 1.4 gram of water.

The hair bleaching composition of Formula 4 was prepared in two steps: at the first step, 80 gram of pyroglutamic acid, 40 gram of arginine, 10 gram of lysine, and 2 gram of diglucosyl gallic acid were mixed together; and at the second step, 1.32 gram of the mixture resulted at the first step was mixed with 98.6 gram of Clairol Professional BW2 Powder Lightener by Coty, Inc. and water in QS amount.

Therefore, based on the persulfate load of the Clairol Professional BW2 Powder Lightener, the persulfate loads of Formula 3 and Formula 4 are the same, about 44.37%.

4.2 Application

Tress Preparation

For Experiments IX and X a level 8 hair swatch measuring 1" wide, 6" length", and approximately 3 g of hair (IHIP, NY) was divided into three equivalent sections. One section was retained as untreated and the other two were treated as described.

Experiment IX

The hair bleaching composition of Formula 3 (5 g) and Salon Care 30 Volume Clear Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was repeated once so that the strands were bleached a total of two times in succession. The treated hair fibres were stored for 24 hours in a humidity chamber before the Elastic Modulus tests. All treated hair fibres showed sufficient color loss.

Experiment X

The hair bleaching composition of Formula 4 (5 g) and Salon Care 30 Volume Clear Developer (10 g) were mixed together. The freshly produced mixture was evenly applied to dry strands of hair at the amount of 5 g of mixture per gram of hair. Once the strands had been bleached for 45 minutes at 37° C., they were washed for 2 minutes using water and dried using a hairdryer on medium heat.

This bleaching process was repeated once so that the strands were bleached a total of two times in succession. The treated hair fibres were stored for 24 hours in a humidity chamber before the Elastic Modulus tests. All treated hair fibres showed sufficient color loss.

4.3. Determination of Changes in Elastic Modulus (EMod)

From each tress 40 individual hair fibres were prepared for tensile analysis using brass crimps and a Diastron AAS 1600 (Diastron Ltd, UK) to thread and crimp the hair. The mean cross-sectional area of each fibre was determined using a laser micrometer FDAS 770 unit (Diastron Ltd, UK) at 24° C. and 55% relative humidity (RH).

All hair fibres were soaked for 1 hour in water before the test. They then were stretched (0-1.5% extension) with a Diastron MTT 686 instrument with control unit UV1000 (Diastron Ltd, UK) and the final results were calculated by software analysis (UvWin 2.35.0000, Diastron, Ltd, UK). The changes in Elastic Modulus then were recorded in the following table. It is understood that higher EMod value corresponds to stronger hair fibres. Thus the negative EMod value may be related to lower hair fibre strength resulted from the hair lightening process. The more negative the value is, the more strength loss may be caused during the hair lightening process.

The results in Table 5 clearly indicate that hair fibres in Experiment X show much less strength loss than that of hair fibres treated by Experiment IX, respectively.

TABLE 5

Changes in Elastic Modulus (EMod) Before and After Bleaching

|  | Formula IX | Experiment X |
|---|---|---|
| ΔEMod (GPa) | −1.71 | −1.42 |

While particular compositions of the invention have been described, it would be obvious to those skilled in the art that various modifications can be made without departing from the spirit and scope of the invention. The appended claims are intended to cover all such modifications.

What is claimed is:

1. A method for bleaching hair, comprising:
   a) mixing a bleaching composition with a developer composition;
   b) applying the mixture of the step (a) onto hair and allowing the mixture to remain for no more than two hours;
   c) rinsing the mixture of the step (a) from hair;
   wherein the bleaching composition comprising at least one gallic acid derivative; at least one amino acids and/or at least one amino acid derivative; at least one oxidizing agent; and optionally, at least one hair care and/or hair treatment agent.

2. The method for bleaching hair of claim 1, wherein the at least one gallic acid derivative has the following formula (I),

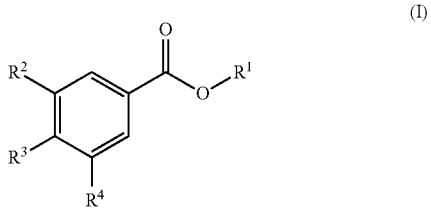

(I)

wherein R1 represents a hydrogen atom, an alkali metal, an alkaline earth metal, an ammonium salt, or an alkyl or alkenyl group having from 1 to 18 carbon atoms; and wherein R2, R3, and R4 independently represent a hydrogen atom, an hydroxyl group, an alkoxy group having from 1 to 18 carbon atoms, a polyoxyethylene group, a polyoxypropylene group, or a residue of a monosaccharide, a disaccharide or an oligosaccharide.

3. The method for bleaching hair of claim 1, wherein at least one gallic acid derivative comprises the gallic acid derivative selected from gallic acid-3, 5-diglucoside; gallic acid-3, 4-diglucoside; methyl gallate-3,5-diglucoside; ethyl gallate-3,5-diglucoside; propyl gallate-3,5-diglucoside; butyl gallate-3,5-diglucoside; gallic acid-3,5-dimannoside; sodium gallate-3,5-diglucoside; ammonium gallate-3,5-diglucoside, gallic acid-3-glucoside, methyl galate-3-glucoside, ethyl galate-3-glucoside, propyl galate-3-glucoside, gallic acid-4-glucoside, sodium gallic acid-3-glucoside, ammonium gallic acid-4-glucoside, gallic acid-3-mannoside, gallic acid-4-mannoside, methyl galate-4-mannoside, and mixtures thereof.

4. The method for bleaching hair of claim 1, wherein the at least one gallic acid derivative comprises diglucosyl gallic acid.

5. The method for bleaching hair of claim 1, wherein the at least one gallic acid derivative is present from 0.0001% to 10%, based on the total weight of the hair bleaching hair.

6. The method for bleaching hair of claim 1, wherein the at least one amino acid and/or at least one amino acid derivative is present from 0.01% to 10% based on the total weight of the hair bleaching hair.

7. The method for bleaching hair of claim 1, wherein the at least one oxidizing agent is selected from the group consisting of persulfate salts, percarbonate salts, and mixtures thereof.

8. The method for bleaching hair of claim 7, wherein the at least one oxidizing agent is selected from the group consisting of sodium persulfate, potassium persulfate, ammonium persulfate, and mixtures thereof.

9. The method for bleaching hair of claim 8, wherein the persulfate load of the hair bleaching hair is from about 1% to about 85% based on the total weight of the hair bleaching hair.

* * * * *